US005620921A

United States Patent [19]

Sullivan

[11] Patent Number: 5,620,921
[45] Date of Patent: Apr. 15, 1997

[54] OCULAR ANDROGEN THERAPY IN SJOGREN'S SYNDROME

[75] Inventor: David A. Sullivan, Acton, Mass.

[73] Assignee: The Schepens Eye Research Institute, Inc., Boston, Mass.

[21] Appl. No.: 124,842

[22] Filed: Sep. 21, 1993

Related U.S. Application Data

[63] Continuation of Ser. No. 871,657, Apr. 21, 1992, abandoned.
[51] Int. Cl.$^6$ .................................................. A61K 31/56
[52] U.S. Cl. ............................................. 514/178; 514/178
[58] Field of Search ..................................... 514/178, 912

[56] References Cited

U.S. PATENT DOCUMENTS

| | | | |
|---|---|---|---|
| 2,861,920 | 11/1958 | Dale et al. | 167/65 |
| 3,962,430 | 6/1976 | O'Neill | 424/185 |
| 4,082,881 | 4/1978 | Chen et al. | 424/241 |
| 4,154,820 | 5/1979 | Simoons | 424/175 |
| 4,474,751 | 10/1984 | Maslom et al. | 424/78 |
| 4,474,811 | 10/1984 | Masuda et al. | 424/317 |
| 4,478,818 | 10/1984 | Shell et al. | 424/14 |
| 4,581,226 | 4/1986 | Dillon | 424/49 |
| 4,617,299 | 10/1986 | Knepper | 514/178 |
| 4,642,305 | 2/1987 | Johansson et al. | 514/182 |
| 4,774,236 | 9/1988 | Cook et al. | 514/176 |
| 4,812,448 | 3/1989 | Knopper | 514/178 |
| 4,861,763 | 8/1989 | Cook et al. | 514/172 |
| 4,863,912 | 9/1989 | Southren et al. | 514/177 |
| 4,866,049 | 9/1989 | Maumenee et al. | 514/169 |
| 4,951,683 | 8/1990 | Davis | 128/734 |
| 4,954,490 | 9/1990 | Cook et al. | 514/176 |

OTHER PUBLICATIONS

Holly, "Tear film physiology", Internat. Ophthalmol. Clin. 27:2-6 (1987).
Whitcher, "Clinical diagnosis of the dry eye", Internat. Ophthalmol. Clin. 27:7-24 (1987).
Lamberts, "Keratoconjunctivitis sicca", In The Cornea, Scientific Foundations and Clinical Practice (G. Smolin, and R.A. Theft, Eds.), pp. 293-308, Little, Brown and Co, Boston, MA (1983).
Sato et al., "Impact of Androgen Therapy in SJögren's Syndrome: Hormonal Influence on Lymphocyte Populations and to Expression in Lacrimal Glands of MRL/MP-Ipr/Ipr Mice", Invest. Ophthal. Vis. Sci 33: 193-201 (1992).
Sullivan et al., "Influence of Steroids and Immunosuppressive Compounds on Tear IgA levels in a Mouse Model of Sjögren's Syndrome", Invest. Ophthal. Vis. Sci. 33: 845A (1992).
Sato et al., "Effect of Testosterone on the Lymphocyte Distribution in, and IgA Output of, Lacrimal Glands in a Mouse Model of Sjögren's Syndrome", Invest. Ophthal. Vis. Sci. 32: 727A (1991).
Verheul et al., "Effects of Tibolone, Lynestrenol, Ethylestrenol, and Desogestrel on Autoimmune Disorders in NZB/W Mice," Clin. Immunol. Immunopathol. 38:198, 1986.
Jungers et al., "Hormonal Modulation in Systemic Lupus Erythematosus," Arthritis Rheum. 28:1243, 1985.

Lavalle et al., "Correlation study between prolactin and androgens in male patients with systemic lupus erythematosus," J. Rheumatol. 14:268, 1987.
Grossman, "Are there underlying immune–neuroendocrine interactions responsible for immunological sexual dimorphism?", Progress in NeuroEndocrinImmunology 3:75, 1990.
Sullivan et al., "Hormonal influence on the secretory immune system of the eye: endocrine impact on the lacrimal gland accumulation and secretion of IgA and IgG," J. Steroid Biochem. 34:253, 1989.
Schuurs et al., "Effect of gender and sex steroids on the immune response," J. Steroid. Biochem. 35:157, 1990.
Michalski et al., "Effect of androgen therapy on survival and suppressor cell activity in aged NZB/NZW F1 mice," Clin. exp. Immunol. 52:229, 1983.
Holdstock et al., "Effects of testosterone, oestradiol and progesterone on immune regulation," Clin. Exp. Immunol. 47:449, 1982.
Ahmed et al., "Effects of short–term administration of sex hormones on normal and autoimmune mice", J. Immunol. 134:204, 1985.
Morton et al., "Androgen Sensititive and autoimmune disease, I. Influence of sex and testosterone on the humoral immune response of autoimmune and non–autoimmune mouse strains to sheep erythrocytes," Immunology 44:661, 1981.
Brick et al., "Hormonal modulation of responses to thymus–independent and thymus–dependent antigens in autoimmune NZB/W–+/+ mice," J. Immunol. 134:3693, 1985.
Talal et al., "Interleukin 2, T. cell receptor and sex hormone studies in autoimmune mice", J. Rheum. (supl. 13) 14:21, 1987.
Sthoeger et al., "Regulation of the immune response by sex hormones. I. In vivo effects of estradiol and testosterone on pokeweed–mitogen–induced human B–cell differentiation," J. Immunol. 141:91, 1988.
Carlsten et al., "Oestradiol–and testosterone–mediated effects on the immune system in normal and autoimmune mice are genetically linked and inherited as dominant traits," Immunology 68:209, 1989.
Schuurs et al., "Experimental work with anabolics in autoimmunity models," Acta Endocrinol. (suppl). 271:97, 1985.
Appelmans, Arch. Ophthalmologie 81:577, 1948.
Bruckner, "Über einen erfolgreich mit Perandren behandelten Fall von Sjögren'schem Symptomenkomplex," Ophthalmologics 110:37, 1945.

(List continued on next page.)

Primary Examiner—Zohreh Fay
Attorney, Agent, or Firm—Weingarten, Schurgin, Gagnebin & Hayes

[57] ABSTRACT

The topical application to the ocular surface or adjacent regions of the eye of a preparation containing a therapeutic amount of an androgen or androgen analogue is disclosed as a method of relieving the chronic and acute manifestation of dry eye symptoms in Sjögren's syndrome.

12 Claims, No Drawings

OTHER PUBLICATIONS

Lebranchu et al., "Thymic function in NZB mice. IV. Role of thymus secretion and sex factors in the expression of suppression," Clin. Immunol. Immunopathol. 23:563, 1982.

Smith et al., "Autoimmunity–a perspective," Ann. Rev. Immunol. 1:175, 1983.

Talal et al., "Hormonal approaches to immunotherapy of autoimmune diseases," Ann. New York Acad. Sci. 475:320, 1986.

Eidenger et al., "Studies of the regulatory effects of the sex hormones on antibody formation and stem cell differentiation," J. Exp. Med. 136:1098, 1972.

Olsen et al., "Studies of immunological function in mice with defective androgen action. Distinction between alterations in immune function due to hormonal insensitivity and alteration due to other genetic factors," Immunology 73:52, 1991.

Savino et al., "Thymic hormone containing cells–IX. Steroids in vitro modulate thymulin secretion by human and murine thymic epithelial cells," J. Steroid Biochem. 30:479, 1988.

Weinstein et al., "Testosterone effect on bone marrow, thymus and suppressor T cells in the (NZB/NZW) F1 mice: its relevance to autoimmunity," J. Immunol. 126:41, 1980.

Kovacs et al., "Androgen receptors in human thymocytes," J. Immunol. 139:490, 1987.

Berczi et al., "Effects of hypophysectomy on immune function," In Psychonhuroimmunology II, Ader et al., eds., Academic Press, San Diego, CA, p. 339, 1990.

Berczi et al., "Neurohormonal–immune interaction." In Functional Endocrine Pathology, Kovaks et al., eds., Blackwell Scientific Publications, Inc., United Kingdom, p. 990, 1990.

Bartlett et al., "Development of autoimmunity in MRL/lpr mice and the effects of drugs on this murine disease", Scand. J. Rheumatol. Suppl. 75:290–299 (1988).

Wilson et al., Eds., "Williams Textbook of Endocinology," WB Saunders Company, Philadelphia (1985).

Knepper et al., "Effects of dexamethasone, progesterone, and testosterone on IOP and GaGs in the rabbit eye", Invest. Ophthalmol. Vis. Sci. 26:1093–1100 (1985).

Vida, "Androgens and Anabolic Agents," *Academic Press*, New York (1969).

Cavallero, "Relative effectiveness of various steroids in an androgen assay using the exorbital lacrimal gland of the castrated rat", Acta Endocrinol. (Copenh.), 55:119–131 (1967).

Lemp, "Recent developments in dry eye management", Ophthalmology 94:1299–1304 (1987).

Lubniewski et al., "Diagnosis and management of dry eye and ocular surface disorders", Ophthalmol. Clin. N.A. 3:575–594 (1990).

Kaswan, "Cyclosporine drops: a potential breakthrough for dry eye", Res. Prev. Blindness Writers Seminar, pp. 18–20 (1989).

Tabbara, "Sjögren's Syndrome", In The Cornea, Scientific Foundations and Clinical Practice (G. Smolin, and R.A. Thoft, Eds), pp. 309–314, Little, Brown and Co. Boston, MA (1983).

Moutsopoulos et al., "Immunologic abnormalities in Sjögren's syndrome", In Sjögren's Syndrome. Clinical and Immunological Aspects (N, Talal, H.M. Moursopoulos, and S.S. Kassan, Eds. J. pp. 258–265, Springer Verlag, Berlin (1987).

Talal, et al., "Treatment of Sjögren's syndrome", In Sjögren's Syndrome, Clinical and Immunological Aspects (N. Talal, H.M. Moutsopoulos, and S.S. Kassan, Eds. 1, pp. 291–295, Springer Verlag, Berlin (1987).

Kincaid, "The eye in Sjögren's Syndrome", In Sjögren's Syndrome, Clinical and Immunological Aspects (N. Talal, H.M. Moutsopoulos, and S.S. Kassan, Eds. 1, pp. 25–33, Springer Verlag Berlin (1987).

Daniels, et al., "Diagnosis and differential diagnosis of Sjögren's syndrome", In Sjögren's Syndrome, Clinical and Immunological Aspects (N. Talal, H.M. Moutsopoulos, and S.S. Kassan, Eds. 1 pp. 193–199, Springer Verlag, Berlin (1987).

Daniels et al., "Histopathology of Sjögren's syndrome", In Sjögren's Syndrome, Clinical and Immunological Aspects (N. Talal, H.M. Moutsopoulos, and S.S. Kassan, Eds 1, pp. 41–52, Springer Verlag, Berlin (1987).

Besedovsky et al., "Immune–neuroendocrine interactions", J. Immunol., 135:750–754 (1985).

Berczi, "Pituitary Function and Immunity", pp. 1–347, CRC Press, Boca Raton, Fla. (1986).

Berczi et al., "Hormones and Immunity" pp. 1–332, MTP Press, Ltd., Lancaster, England (1987).

Jancovic et al., "Neuroimmune interactions", Ann. N.Y. Acad. Sci. 496, New York Acad. Sci., New York (1987).

Weigent et al., "Interactions between the neuroendocrine and immune systems: common hormones and receptors", Immunol Rev 100:79–108 (1987).

Freier, Ed., "The Neuroendocrine–Immune Network", pp. 1–266, CRC Press, Boca Raton, Fla (1990).

Hadden et al., Eds., "Interactions Among Central Nervous System, Neuroendocrine and Immune Systems," pp. 1–464, Pythagora Press, Rome (1989).

Ader et al., Eds.. "Psychoneuro–immunology, 2nd Edition," pp. 1–1248, Academic Press, San Diego, CA (1991).

Ader et al., "Interactions between the brain and immune system", Ann. Rev. Pharmacol. Toxicol. 30:561–602 (1990).

Jabs et al., "Murine models of Sjogren's syndrome"; Invest Ophthalmol Vis Sci 29:1437 (1988).

Jonsson et al., Immunohistochemical characterization of sialadenitis in NZB×NZW F1 mice"; Clin. Immunol. Immunopathol. 42:93–101 (1987).

Connolly et al., "The effect of danazol in the MRL/lpr mouse model of autoimmune disease"; Agents Actions 25:164–170 (1988).

Mountz et al., "CS–A therapy in MRL–lpr/lpr mice: amelioration of immunopathology despite autoantibody production", J. Immunol. 138:157–163 (1987).

Hazelton et al., "Hormonal manipulation of the immune response in systemic lupus erythematosus: a drug trial of an anabolic steroid, 19–nortestosterone", Annals Rheum. Dis. 42: 155–157 (1983).

Lahita, "Sex hormones, Sjögren's syndrome and the immune response", The Moisture Seekers Newsletter 8:1 (1991).

Comsa et al., "Hormonal Coordination of the immune response", Rev. Physiol. Biochem. Pharmacol. 92:115–191 (1982).

Grossman, "Regulation of the immune system by sex steroids", Endocr. Rev., 5:435–455 (1984).

Munck et al., "Physiological functions of glucocorticoids in stress and their relation to pharmacological actions", Endocr. Rev., 5:25–44 (1984).

Bizzarro et al., "Influence of testosterone therapy on clincal and immunological features of autoimmune diseases associated with Klinefelter's syndrome", J. Clin. End. Metab. 64:32–36 (1987).

Hoffman et al., "Sjögren's syndrome in MRL/l and MRL/n mice", Arthritis Rheum. 27:157–165 (1984).

Jabs et al., "Ocular inflammation in autoimmune MRL/Mp mice"; Invest. Ophthalmol. Vis. Sci. 26:1223–1229 (1985).

Kessler, "A laboratory model for Sjögren's syndrome"; Am. J. Pathol. 52:671–678 (1968).

Celenligil et al., "Secretory immune system and mucosal immunohistology in Sjögren's syndrome"; Adv. Exp. Biol. Med. 216B:1641–1648 (1987).

Drosos et al., "Nandrolone decanoate (deca–durabolin) in primary Sjögren's syndrome: a double blind study", Clin Exp. Rheum. 6:53–57 (1988).

Hene et al, "Lack of clinical effect of the androgenic steroid nandrolone on primary Sjögren's syndrome (PSS)", Clin. Exp. Rheum. 9:338 (1991).

Steinberg et al., "Effects of thymectomy or androgen administration upon the autoimmune disease of MRL/Mp-Ipr/Ipr mice", J. Immunol. 125:871–873 (1980).

Brick et al., "Hormone control of autoantibodies to calf thymus nuclear extract (CTE) and DNA, in MRL–Ipr and MRL–+/+mice", Clin. Immunol. Immunopathol. 46:68–81 (1988).

Nelson et al., "Sex steroids, autoimmunity, and autoimmune diseases", In Hormones and Immunity (I. Berczi, and K. Kovacs, Eds.), pp. 93–119, MTP Press Limited, Lancaster, England (1987).

Shear et al., "Effects of castration and sex hormones on immune clearance and autoimmune disease in MRL/MP–Ipr/Ipr and MRL/Mp–+/+mice", Clin. Immunol. Immunopathol. 26:361–369 (1983).

Ansar/Ahmed et al., "Beneficial effect of testosterone in the treatment of chronic autoimmune thyroiditis in rats", J. Immunol. 136:143–147 (1986).

Allen et al., "Sex hormonal effects on the severity of streptococcal cell wall induced polyarthritis in the rat", Arthritis Rheum., 26:560–565 (1983).

Ahn et al., "Danazol for the treatment of idiopathic thrombocytopenic purpura", N. Engl. J. Med. 308:1396–1399 (1983).

Sullivan et al., "Hormonal influence on the secretory immune system of the eye", In The Neuroendocrine–Immune Network (I. Berczi, Ed.), pp. 199–238, CRC Press, Boca Raton, Fla, (1990).

MacDonald et al., Eds, "Advances in Mucosal Immunology," pp. 1–948, Kluwer Academic Publishers, London, England (1990).

Ariga et al., "Androgen control of autoimmune expression in lacrimal glands of MRL/Mp-Ipr/Ipr mice", Clinical Immunology and Immunopathology 53:499–508 (1989).

Vendramini et al., "Testosterone–induced suppression of autoimmune disease in lacrimal tissue of a mouse model (NZB/NZW F1) of Sjögren's Syndrome", Invest. Ophthalmol. Vis. Sci. 32:3002–3006 (1991).

Ahmed et al., "Estrogen induces the development of autoantibodies and promotes salivary gland lymphoid infiltrates in normal mice"; J. Autoimmunity 2:543–552 (1989).

Frost–Larsen et al., "Sjögren's syndrome treated with bromhexine: a randomized clinical study; Br. Med. J. 1:1579–1581 (1978).

Gilbard et al., "Stimulation of tear secretion and treatment of dry–eye disease with 3–isobutyl–1–methylxanthine"; Arch. Ophthalmol. 109:672–676 (1991).

Manthorpe et al., "Mucosolvan in the treatment of patients with primary Sjögren's syndrome"; Acta Ophthalmol. (Copenh) 62:537–541 (1984).

Kriegbaum et al., "A follow–up study of the progress of keratoconjunctivitis sicca and response to treatment in primary Sjödgren's syndrome", Scand. J. Rheumatol. 18:193–196 (1989).

Raveche et al., "Sex hormones in autoimmunity", In Pituitary Function and Immunity (I. Berczi, Ed.), pp. 283–301, CRC Press, Boca Raton, Florida (1986).

Ahmed et al., "Sex hormones and the immune system–part 2. Animal data"; Bailliere's Clin. Rheum, 4:13–31 (1990).

Roubinian et al., "Effect of castration and sex–hormone treatment on survival, anti–nucleic acid antibodies, and glomerulonephritis in NZB/NZW F1 mice", J. Exp. Med. 147:1568–1583 (1978).

Melez et al., "Therapeutic studies in New Zealand mice. VII. Successful androgen treatment of NZB/NZW F1 females of different ages", Arthritis Rheum. 23:41–47 (1980).

Garry et al., "Detection of a human intracisternal A–type retroviral particle antigenically related to HIV", Science 250:1127–1129 (1990).

Fox, "Epstein–Barr virus and human autoimmune diseases: possibilties and pitfalls", J. Vir. Meth. 21:19–27 (1988).

Maini, "The relationship of Sjögren's syndrome to Rheumatoid Arthritis", In Sjogren's Syndrome. Clinical and Immunological Aspects (N. Talal, H.M. Moutsopoulos, and S.S. Kassan, Eds.), pp. 165–176, Springer Verlag, Berlin (1987).

Venables et al., "Persistence of Epstein–Barr virus in salivary gland biopsies from healthy individuals and patients with Sjögren's syndrome", Clin. Exp. Immunol. 75:359–364 (1989).

Tabbara et al., "Alternate–day steroid therapy for patients with primary Sjögren's syndrome", Annals Ophthalmol. 15:358–361 (1983).

Prijot et al., "Essai de traitment hormonal de la keratocon–jonctivite seche", Bull, Soc. Belge Ophtalmol. 162:795–800 (1972).

Drosos et al., "Cyclosporin A therapy in patients with primary Sjögren's syndrome: results at one year", Scand. J. Rheum. Suppl. 61:246–249 (1986).

Nasu et al., "Post–mortem prevalence of lymphocytic infiltration of the lacrymal gland: a comparative study in autoimmune and non–autoimmune diseases", J. Pathology 143:11–15 (1984).

Carlsten et al., "Oestrogen is a potent disease accelerator in SLE–prone MRL Ipr/Ipr mice", Clin. Exp. Immunol. 80:467–473 (1990).

Alexander, "Neuromuscular complications of primary Sjögren's syndrome"; In Sjögren's Syndrome. Clinical and Immunological Aspects (N. Talal, H.M. Moutsopoulos and S.S. Kassan Eds.) pp. 61–82, Springer Verlag, Berlin (1987).

Daniels, "Sjogren's syndrome–in a nut shell", Sjögren's Syndrome Foundation Inc. Report, Port Washington, NY (1990).

Talal et al., "Sex hormones and autoimmune disease: a short review", Int. J. Immunotherapy 3:65–70 (1987).

Ansar Ahmed et al., "Sex hormones, immune responses and autoimmune diseases", Am. J. Pathol. 121:531–551 (1985).

Burns, "Persistent cytomegalovirus infection. The etiology of Sjögren's syndrome", Med. Hypotheses 10:451–460 (1983).

Fox, et al., "Detection of Epstein–Barr virus–associated antigens and DNA in salivary gland biopsies from patients with Sjögren's syndrome", J. Immunol. 137:3162–3168 (1986).

Pflugfelder et al., "Epstein–Barr virus infection and immunological dysfunction in patients with aqueous tear deficiency", Ophthalmology 97:313–323 (1990).

Pepos et al., "Mononuclear cell phenotypes and immunoglobulin gene rearrangements in lacrimal gland biopsies from patients with Sjögren's syndrome", Ophthalmology 97:1599–1605 (1990).

Green et al., "Exocrinopathy resembling Sjögren's syndrome in HTLV-1 *tax* transgenic mice", Nature 341:72–74.

Stead et al., "Neuropeptide regulation of mucosal immunity", Immunol. Rev. 100:333–359 (1987).

Golsteyn et al., "Review: The role of the thymic–hypothalamus–pituitary–gonadal axis in normal immune processes and autoimmunity", J. Rheum. 14:982–990 (1987).

Physicians' Desk Reference, 46th edition. *Medical Economics Data,* Montvale, N.J. (1992).

Andrews et al., "Spontaneous murine lupus–like syndromes: Clinical and immunopathological manifestations in several strains", J. Exp. Med. 149:1198–1215 (1978).

Theofilopoulos et al., "Murine models of systemic lupus erythematosus", Adv. Immunol. 37:269–390 (1985).

Gelfand et al., "Treatment of hereditary angioedema with danazol", New Eng. J. Med. 295:1444–1448 (1976).

Jonsson et al. "Effects of immunomodulating treatment on autoimmune sialadenitis in MRL/Mp–lpr/lpr mice", Agents Actions 25:368–374 (1988).

Smith et al., "Cyclophosphamide–induced changes in the MRL–lpr/lpr mouse: Effects upon cellular composition, immune function and disease", Clin. Immunol. Immunopathol. 30:51–61 (1984).

Shiraki et al., "Long term administration of cyclophosphamide in MRL/l mice I. The effects on the development of immunological abnormalities and lupus nephritis", Clin. Exp. Immunol. 55:333–339 (1984).

Invest Ophthalmol vis Sci 1991 Oct; 32 (11):3002–6.

Vandramini et al. See The Medline Abstract 007102117 WPI Acc No: 87–102114/15, Schroder et al.

OCULAR ANDROGEN THERAPY IN SJOGREN'S SYNDROME

Part of the work leading to this invention was made with United States Government funds. Therefore, the U.S. Government has certain rights in this invention.

This application is a continuation of application Ser. No. 07/871,657, filed Apr. 21, 1992, now abandoned entitled: OCULAR ANDROGEN THERAPY IN SJÖGREN'S SYNDROME.

FIELD OF THE INVENTION

This invention relates to treating symptoms of Sjögren's syndrome.

BACKGROUND OF THE INVENTION

The preocular tear film plays an essential role in the maintenance of corneal integrity, the protection against microbial challenge and the preservation of visual acuity (1). These functions, in turn, are critically dependent upon the stability, tonicity and/or composition of the tear film structure, which includes an underlying mucin foundation, a substantial, middle aqueous component and an overlying lipid layer (1,2). Alteration, deficiency or absence of the tear film may lead to intractable desiccation of the corneal epithelium, ulceration and perforation of the cornea, an increased incidence of infectious disease, and ultimately, severe visual impairment and blindness (2,3).

Throughout the world, countless individuals suffer from tear film dysfunctions, which are collectively diagnosed as keratoconjunctivitis sicca (KCS) or, simply, dry eye (1,2). These lacrimal abnormalities may be subdivided into four general categories: (a) aqueous tear deficiencies, which are most frequently responsible for dry eye states, originate from lacrimal gland disorders and include autoimmune disease, congenital alacrima, paralytic hyposecretion or excretory duct obstruction; (b) mucin deficiency, which is observed in various conjunctival cicatrization conditions, such as Stevens-Johnson syndrome, trachoma, pemphigoid, thermal and chemical burns, as well as hypovitaminosis A; (c) lipid abnormalities, which may occur during eyelid inflammation (e.g. chronic blepharitis); and (d) diminished eyelid function (1).

By far, the greatest single cause of KCS worldwide, excluding those countries wherein trachoma remains epidemic, is Sjögren's syndrome (2). This syndrome, which is the second most common autoimmune disease (7,14), occurs almost exclusively in females and is characterized by an insidious and progressive lymphocytic infiltration into the main and accessory lacrimal glands, an immune-mediated, extensive destruction of lacrimal acinar and ductal tissues and the consequent development of persistent KCS (7–10). In primary Sjögren's syndrome, which afflicts about 50% of the patient population, the disease is also associated with an immunological disruption of the salivary gland and pronounced xerostomia. In secondary Sjögren's, the disorder is accompanied by another disease, which is most often rheumatoid arthritis and less frequently systemic lupus erythematosus (SLE), scleroderma, polymyositis, polyarteritis nodosa, Hashimoto's thyroiditis, chronic hepatobiliary disease, chronic pulmonary fibrosis, purpura hyperglobulinemia or Raynaud's phenomenon (2,11). During the course of Sjögren's syndrome, autoimmune sequelae may also encompass focal lymphocytic adenitis of eccrine and mucosal glands, biliary cirrhosis, sclerosing cholangitis, pancreatitis, atrophic gastritis, interstitial nephritis and pneumonitis, peripheral vasculitis, B cell lymphoma and a diverse array of central and peripheral nervous system and skeletal muscle complications (12,13).

The etiology of Sjögren's syndrome may be due to the interaction of numerous factors, including those of genetic, endocrine, neural, viral and environmental origin (15,16). However, a potential cause may relate to primary infection by, and reactivation of, Epstein-Barr virus (EBV) and/or cytomegalovirus (CMV) (17–20). These herpes viruses are present in lacrimal and salivary glands of Sjögren's patients (17–20) and may induce the inappropriate HLA-DR expression, T helper/inducer cell activation, B cell hyperactivity and autoantibody production evident in these affected tissues (8). However, whether herpes, or even retroviral (21,22), action represents a cause of, or merely an epiphenomenon in, Sjögren's syndrome remains to be determined (23–25).

At present, a perception is that Sjögren's syndrome may be clinically irreversible (7), an autoimmune disease to be controlled, yet not cured (10). In the scientific literature, reports have suggested that systemic or topical administration of estrogens (4), cyclosporine A (6) or glucocorticoids (26) might alleviate the ocular manifestations of this disorder. However, other studies indicate that such pharmaceutical exposures are ineffective (27–29) and, in fact, may accelerate and/or amplify the disease (28,30). Indeed, estrogen action may be involved in the etiology of Sjögren's syndrome (30,31).

Others have suggested that tear stimulants, such as bromhexine (32) or isobutylmethylxanthine (33), might improve ocular symptoms. These drug effects, though, may be subjective (34), susceptible to tachyphylaxis (4) and/or limited by the requirement for functional and responsive lacrimal tissue (4,35).

It has also been proposed that systemic androgen treatment might provide a potential therapy for Sjögren's syndrome and its associated defects. This proposal is based upon the finding that autoimmune disorders commonly display a sexual dichotomy, with estrogens increasing disease severity in females and androgens suppressing autoimmune sequelae in males (15,16,36–38). In fact, systemic androgen therapy has been utilized to effectively diminish autoimmune expression in animals models of SLE, thyroiditis, polyarthritis and myasthenia gravis (15,38–43), as well as the human condition of idiopathic thrombocytopenic purpura (44). However, research has also demonstrated that the systemic administration of androgens to patients with primary or secondary Sjögren's syndrome or SLE is apparently unable to correct various peripheral manifestations of these disorders (49,54,55,62). In addition, systemic androgen treatment of female patients with Sjögren's syndrome exposes these individuals to possible undesirable side effects, including virilization, menstrual irregularities (e.g., amenorrhea), hepatic dysfunction, edema, hematologic abnormalities, behavioral changes and metabolic alterations. Similarly, chronic treatment of males with systemic androgens has been characterized as dangerous (63), because of the numerous potential side effects. For these reasons, a recent report has indicated that systemic androgen therapy is inappropriate for the treatment of the multiple immune dysfunctions in Sjögren's syndrome (63).

Others have suggested that anti-viral compounds may represent a new therapeutic approach for ocular disease in Sjögren's syndrome. Researchers have speculated that such compounds may be effective in counteracting the viral (e.g.,

3

EBV- and/or CMV)-induced infection in lacrimal tissue, that may possibly precipitate the gland's immune-associated dysfunction (17,19,20). The potential efficacy of this strategy, though, is highly speculative: current scientific information does not show definitively that these viruses are directly involved in the pathogenesis or progression of Sjögren's syndrome (23–25).

Therefore, the currently prescribed, therapeutic approach for the management of KCS in Sjögren's syndrome is the frequent application of artificial tear substitutes, which permit lubrication of the eye's anterior surface (3,4,5,9,10). Unfortunately, this therapy does not represent a cure and does not ameliorate the inherent, ocular immunopathology and resulting KCS associated with this chronic, extremely uncomfortable and vision-threatening disease (3).

SUMMARY OF THE INVENTION

The invention generally features a new approach to the management of KCS in Sjögren's syndrome, the topical application to the eye of a preparation containing a therapeutic amount of an androgen or androgen analogue. This method of treatment can alleviate the ocular manifestations of Sjögren's syndrome, the special symptoms that cause great distress, while not exposing the patient to the possible undesirable side effects of systemic treatment.

In one aspect, the invention features a method for treating symptoms of keratoconjunctivitis sicca (KCS) that includes providing a therapeutic agent including an effective amount of an androgen or androgen analogue in a pharmaceutically acceptable substance, and administering said therapeutic agent topically to the ocular surface or immediate vicinity of an eye of a patient.

Preferably, the substance is phosphate buffered saline or a carrier substance such as hyaluronate and the androgen or androgen compound has unusual structural features; or the compound is a testosterone, 4,5α-dihydrotestos-terone, 17β-hydroxy-5α-androstane, or 19-nortestosterone derivative; or the compound is a nitrogen-substituted androgen.

The invention also features the therapeutic composition used in the method of the invention.

Other features and advantages of the invention will be apparent from the following description of the preferred embodiments thereof and from the claims.

DESCRIPTION OF THE PREFERRED EMBODIMENTS

Various androgen compounds, as herein discussed, significantly reduce the magnitude of lymphocyte infiltration in lacrimal tissue of animal models of Sjögren's syndrome. The nature of androgen action on autoimmune expression in lacrimal tissue appears to be unique and lacrimal gland-specific. It also appears that this hormone effect is not linked to a generalized, systemic anti-inflammatory function. Building on these new discoveries, the method of the invention involves a rejection of the classical therapeutic approach to treatment for Sjögren's syndrome, a belief that any administered therapeutic agent must be able to control all aspects of the disease. Because steroid hormones (e.g., glucocorticoids), with solubility characteristics analogous to those of androgens, rapidly gain access to adjacent ocular tissues after topical application (78), it is proposed, instead, that topical application of a therapeutic amount of an androgen or androgen analogue to the eye be used to treat the debilitating ocular manifestations of this disease. Topical application of a therapeutic androgen can provide for symptomatic relief of the worst ocular symptoms of Sjögren's syndrome without the chance of the patient experiencing the undesirable side effects of systemic administration.

During the past decade, it has become increasingly recognized that the endocrine system exerts a tremendous, regulatory impact on immunological expression (15,16,36, 37,45,64,65–68,69,70–76). The precise nature of this endocrine control, though, appears to be both cell- and tissue-specific (45). Thus, depending upon the target, the consequence of hormone action may be stimulation, antagonism or inhibition of immune function. Moreover, individual hormone effects on the immune system are often not generalized. Rather, endocrine influence may actually strengthen, diminish or elicit no effect on immunological activity in different tissues (45). Given this background, it is not surprising that the systemic administration of selected hormones (e.g., androgens) is unable to correct all immune defects in multidimensional, autoimmune disorders, such as Sjögren's syndrome or SLE.

Yet, if appropriate endocrine therapy could be targeted to a specific, responsive tissue, hormone action could safely and effectively ameliorate an immunopathology located in that particular tissue. To relieve the symptoms that cause the most ocular distress in Sjögren's syndrome, that targeted, responsive tissue is the lacrimal gland. Lipophilic, regulatory hormones applied locally on or adjacent to the ocular surface can act directly on accessory and main lacrimal tissues of Sjögren's syndrome patients and suppress the disease-related glandular inflammation in these tissues. This effect would be completely independent of systemic hormone activity. The aim of this immunoendocrine interaction is to: (a) reduce lymphocyte infiltration in adjacent lacrimal tissue and thereby alleviate immune-mediated destruction, and lymphocyte compression, of acinar and ductal cells; (b) permit accessory and/or palpebral lacrimal glands to secrete basal tear volumes; and (c) avoid the side effects that parallel systemic exposure to these hormones. In effect, topical androgen treatment can generate functional regions of lacrimal tissue, thereby enhancing tear output and correcting the dry eye problem.

This pharmaceutical strategy has not been proposed previously. Most probably, this is because the mechanism of androgen action on immune function has been thought to be mediated through, or assisted by, factors from the thymus and hypothalamic-pituitary axis, or else involve direct effects on lymphocytes (37,65,68,77).

A critical requirement for the justification of topical ocular application therapy is to demonstrate that androgens suppress lacrimal gland immunopathology in Sjögren's syndrome. In addition, it is important to show that this androgen action is targeted to lacrimal tissue, and independent of generalized, systemic effects. In the examples given below it is shown that all three of these criteria are met, i.e., that androgens do suppress lacrimal gland immunopathology in Sjögren's syndrome, that androgen action is targeted to lacrimal tissue, and that androgen action is independent of generalized, systemic effects.

EXAMPLE I

Androgen influence on lacrimal gland immunopathology in the MRL/Mp-lpr/lpr mouse model of Sjögren's syndrome (47)

The purpose of the following study was to determine whether androgen therapy might inhibit the progression of, or reverse, autoimmune disease in the lacrimal gland after the onset of Sjögren's syndrome. Towards that end, the study utilized adult, female MRL/Mp-lpr/lpr (MRL/lpr) mice, which are an animal model for both Sjögren's syndrome (50,51) and SLE (79,80). Lacrimal tissues of these mice, as in humans, contain multifocal and extensive lymphocytic infiltrates in perivascular and periductal areas, significant glandular disruption and marked fibrosis (50,51).

Physiological or supraphysiological levels of testosterone were administered systemically, and not topically, because the location of the lacrimal gland in mice is inaccessible from the ocular surface. The results demonstrated that androgens exert a significant impact on autoimmune expression in lacrimal glands of MRL/lpr female mice. Administration of testosterone for 17 or 34 days dramatically reduced the extent of lymphocyte infiltration in lacrimal tissue: this hormone action was time-dependent and involved marked diminutions in both infiltrate size and area. Moreover, hormone therapy appeared to reverse the inflammation-induced disruption of acinar and ductal epithelium. Of interest, there was no significant difference in experimental results between the physiological and supraphysiological doses of testosterone. In contrast, the magnitude of lymphocyte infiltration progressively increased in lacrimal glands of placebo-treated mice during the experimental time course. Testosterone therapy also significantly diminished immunopathology in the submandibular gland, but the extent of this effect was less than found in lacrimal tissue.

EXAMPLE II

Androgen impact on lacrimal gland immunopathology in the NZB/NZW F1 mouse model of Sjögren's syndrome (48)

The objective of this investigation was to assess the efficacy of androgen treatment for lacrimal disease by utilizing another autoimmune, animal model (NZB/NZW F1 [F1] mouse) of Sjögren's syndrome (52,59). As in humans, lacrimal glands of this mouse strain, which displays a fundamental B cell defect, harbor dense, lymphocytic aggregates (50,52), which contain a prevalence of B and helper T cells (58). Moreover, this murine disease is accompanied by focal destruction of acinar and ductal tissue and apparent ocular surface dryness (50,52). In contrast, immune dysfunction in the MLR/lpr model appears to have a different etiology and involves a basic, immunoregulatory disorder of T cells (47).

Autoimmune, female F1 mice were treated systemically with vehicle or varying concentrations of testosterone for 0, 17, 34 or 51 days after the onset of disease; again, the systemic route for hormone treatment was utilized because lacrimal tissue in F1 mice may not be accessed from the ocular surface. Results showed that the extent of lymphocyte infiltration increased dramatically in control mice during the experimental time course. However, testosterone administration induced a significant, time-dependent decrease in lymphocytic accumulation in the lacrimal gland. Following 34 to 51 days of androgen therapy, the magnitude of lymphocyte infiltration had been suppressed 22- to 46-fold, compared to that in placebo-treated tissue. This hormone effect was associated with significant reductions in the number of focal infiltrates, the area of individual foci and the total quantity of lymphocyte infiltration per lacrimal section. In certain groups, testosterone exposure also stimulated a rise in tear volumes, relative to those measured in the same mice prior to treatment. With few exceptions, the impact of physiological and supraphysiological testosterone treatment on lacrimal autoimmune expression in F1 mice was essentially identical, the supression of autoimmune disease.

EXAMPLE III

Effect of androgen therapy in Sjögren's syndrome: hormonal influence on lymphocyte populations and Ia expression in lacrimal glands of MRL/lpr mice Previous research demonstrated that androgen treatment dramatically curtails lymphocyte infiltration in lacrimal glands of mouse models of Sjögren's syndrome. The purpose of this study was to determine whether this androgen action involves the selective suppression of specific lymphocyte populations or Class II antigen (i.e., Ia) expression in lacrimal tissue. Towards this end, autoimmune female MRL/Mp-lpr/lpr mice were administered placebo- or testosterone-containing compounds systemically for 0, 17 or 34 days after the onset of disease. Results showed that androgen exposure exerts both a quantitative and a qualitative influence on inflammatory cell populations in the lacrimal gland of MRL/lpr mice. Thus, testosterone, but not placebo, treatment induced a precipitous decrease in the total number of T cells, helper T cells, suppressor/cytotoxic T cells, Ia-positive lymphocytes and B cells. Androgen administration also significantly diminished the lacrimal density, as well as the frequency, of $B220^+$ (i.e., possibly immature T) cells.

These findings, when compared with other observations (45,47, 48,56), suggest that testosterone's anti-inflammatory activity may be unique and lacrimal gland-specific. First, the androgen-induced immunosuppression in lacrimal tissue does not extend to peripheral lymph nodes (56,57), indicating that this steroid hormone does not cause a generalized depression in lymphocyte migration to, or proliferation in, systemic or mucosal sites. Second, testosterone exposure reduces the magnitude of lymphocytic infiltration in submandibular glands of MRL/lpr mice (47), but the nature of this hormonal influence may be unlike that found in lacrimal tissue, and the overall susceptibility of salivary focal infiltrates to androgens and pharmacological agents appears quite different from that found in lacrimal tissue (47). Third, androgens exert significant control over immunological functions in lacrimal glands, but not necessarily those of salivary or systemic tissues (45).

EXAMPLE IV

Impact of steroids and immunosuppressive agents on lacrimal autoimmune disease in the MRL/lpr mouse model of Sjögren's syndrome The objective of the following experiments was to determine whether other steroid hormones or immunosuppressive agents might duplicate the effect of testosterone on lacrimal gland autoimmunity. Female MRL/lpr mice were treated with systemic vehicle, steroids or immunosuppressive compounds for 21 days after disease onset. The pharmaceutical agents evaluated in this study included: (a) testosterone, which, has been shown to significantly reduce lacrimal gland inflammation; (b) 19-nortestosterone, an anabolic androgen with attenuated virilizing activity; (c) danazol, a synthetic steroid, which is utilized in the treatment of certain immune diseases in humans (81) and is known to diminish specific, peripheral immune defects in MRL/lpr mice (60); (d) 17B-estradiol, a female sex steroid, which has been hypothesized as a potential treatment for ocular disease in Sjögren's syndrome (4); (e) a synthetic, non-androgenic steroid, which apparently suppresses lymphocyte infiltration in salivary glands of F1 mice and corrects other systemic autoimmune defects; (f) cyclosporine A, an anti-inflammatory agent, which ameliorates specific, peripheral immune dysfunctions in MRL/lpr mice (61) and has been proposed as an effective therapeutic agent for lacrimal disease and KCS in Sjögren's syndrome (6); (g) dexamethasone, a potent anti-inflammatory glucocorticoid, that has been suggested as a possible therapeutic agent for lacrimal immunopathology in Sjögren's syndrome (26); and (h) cyclophosphamide, an immunosuppressive agent, that decreases various autoimmune sequelae in systemic (83–85) and salivary (59,82) sites in MRL/lpr mice. The comparative results demonstrated that the suppressive influence of testosterone on focal infiltrate area, number of foci and percentage lymphocyte infiltration in lacrimal tissue was duplicated by the administration of the anabolic androgen, 19-nortestosterone, or cyclophosphamide, but not by therapy with estradiol, danazol, the synthetic non-androgenic steroid, cyclosporine A, or dexamethasone. In addition, testosterone, 19-nortestosterone and cyclophosphamide, as well as dexamethasone, reduced lymphocyte infiltration in the submandibular gland. However, neither androgen interfered with the pronounced inflammation of lymphatic tissues, including the spleen, and superior cervical and mesenteric lymph nodes. Androgen treatment alone also stimulated an increase in the lacrimal gland output of IgA antibodies into tears; these antibodies, which protect the ocular surface against bacterial colonization, vital attachment, parasitic infestation and fungal- or toxin-induced impairment (46), are typically diminished in mucosal sites in Sjögren's syndrome (53).

Overall, these combined findings demonstrate that androgens, or their anabolic analogues, suppress autoimmune expression in lacrimal glands of animal models of Sjögren's syndrome. Androgen action also appears to represent a tissue-specific response independent of generalized, systemic effects, thus justifying topical ocular therapeutic application. Cyclophosphamide, the only non-androgen to reduce lymphocyte infiltration in lacrimal tissue upon systemic administration, is not believed to be appropriate for topical therapy in humans because of its mode of action. This alkylating agent, which is thought to suppress autoimmune function by a direct modification of cellular DNA, must first be metabolized by the liver before becoming active. Therefore, cyclophosphamide would not be capable of local action upon topical application.

USE

Topical application of androgens or their analogues to patients with Sjögren's syndrome or other autoimmune diseases of the lacrimal gland can directly suppress the immunopathological defects in accessory lacrimal tissue and the main lacrimal gland's palpebral lobe, which is adjacent to the ocular surface. Selection of the most appropriate therapeutic compounds will depend upon a given hormone's immunological activity, potential side effects and form of administration. For example, topical testosterone may be quite effective in reducing lacrimal inflammation, and its methylated analogue appears to have no toxic side effects on parameters such as intraocular pressure (87). However, utilization of testosterone as a pharmaceutical agent may be contraindicated: this hormone's metabolism, in various peripheral tissues, may involve aromatization to estrogens (86), which may exacerbate the ongoing autoimmune disease. In addition, with regards to administration, if the androgen is to be complexed to a carrier vehicle (e.g., hyaluronate), then a nitrogenated analogue might be indicated.

Therefore, the efficacy of a variety of modified and/or anabolic androgens in suppressing lacrimal gland autoimmune expression in female MRL/lpr mice was compared. Animals were administered vehicle or designated androgens systemically for 6 weeks after the onset of disease. The androgens examined in this test included: (a) testosterone; (b) dihydrotestosterone (also termed allodihydrotestosterone, androstano-lone, stanolone, $5\alpha$-dihydrostestosterone); (c) fluoxymesterone; (d) stanozolol; (e) nortestosterone propionate; (f) dehydroepi-androsterone (an androgen precursor, also termed androstenolone, dehydroisoandrosterone, DHEA, transdehydroandrosterone); (g) oxandrolone; (h) methyldihydrotestosterone (also termed methylandrostanolone); (i) oxymetholone; (j) $5\alpha$-androstan-$17\beta$-ol-3-oxime; (k) $5\alpha$-androstan-$17\alpha$-ol-3-one-acetate; (l) $2,(5\alpha)$-androsten-$17\beta$-ol; (m) $5\alpha$-androstan-$2\alpha$-methyl-$17\beta$-ol-3-one; and (n) methyltestosterone.

The rationale for comparing the immunological activity of this specific array of androgenic compounds was multifold:

First, these hormones are representative of the major structural subclasses of androgens, as disclosed in Vida (88), hereby incorporated by reference. The subclasses include (a) androgenic compounds with unusual structural features (e.g., $17\alpha$-methyl-$17\beta$-hydroxy-2-oxa-$5\alpha$-androstan-3-one, also termed oxandrolone); (b) testosterone derivatives (e.g., methyltestosterone); (c) $4,5\alpha$-dihydrotestosterone derivatives (oxymetholone); (d) $17\beta$-hydroxy-$5\alpha$-androstane derivatives containing a ring A unsaturation, excluding testosterone derivatives (e.g., $2,(5\alpha)$-androsten-$17\beta$-ol); and (e) 19-nortestosterone derivatives (e.g., 19-nortestosterone propionate). It may be that certain structural features impart more optimal immunosuppressive characteristics, which would be of benefit in selecting specific androgens for human use.

Second, relative to standards (typically testosterone), these androgens include compounds displaying: (a) augmented androgenic (i.e., virilizing) activity coupled with an even larger increase in anabolic activity (e.g., fluoxymesterone); (b) enhanced anabolic action with unchanged androgenic effects (e.g., oxymetholone, dihydrotestosterone); (c) decreased androgenic ability with unchanged anabolic activity (e.g., 19-nortestosterone propionate); and (d) decreased androgenic capacity paralleled by increased anabolic activity (e.g., oxandrolone, stanozolol). Thus, the analysis should identify an androgen with far more anabolic, than virilizing, activity to be utilized for the treatment of ocular manifestations of Sjögren's syndrome (e.g., oxandrolone possesses 322% of the anabolic and 24% of the androgenic activity of methyltestosterone (88)). Of course, it is possible that anabolic effects, per se, may not be involved in androgen suppression of lacrimal autoimmune symptoms. However, the results with 19-nortestosterone in MRL/lpr mice demonstrate that this anabolic androgen, which has significantly reduced androgenic activity in lacrimal tissue (89), was equally as effective as testosterone in abrogating lymphocyte infiltration in the lacrimal gland.

Third, these compounds contain a nitrogen-substituted androgen, $5\alpha$-androstan-$17\beta$-ol 3-oxime, which is created by the substitution of a nitrogen derivative for the 3-ketone function in dihydrotestosterone (very potent androgen) (88). This substitution does not inhibit androgen activity (88) and may permit steroid binding to hyaluronate for topical administration. Of interest, a variety of other nitrogenated androgens have been shown to express increased anabolic, but decreased androgenic, activity. These compounds typically contain 3-substitutions, but not nitrogen incorporation in the steroid ring structure, which appears to abolish androgen action (88).

The results of testing the effect of the representative compounds were that all androgen classes, whether parental, modified or anabolic analogue, were effective in suppressing lacrimal gland autoimmune expression, although to various degrees. With further routine additional testing, the most appropriate therapeutic compound for a specific application can be determined.

Androgen therapy, which can be administered in the form of drops (e.g., free hormone, or complexed with carrier substances, such as hyaluronate) or ointment, should not require frequent applications, considering the mechanism and duration of androgen/cell interactions. The administration of a specific compound would be by routine methods in pharmaceutically acceptable substances, including buffer solutions (e.g., phosphate buffered saline) or inert carrier compounds, to the ocular surface or adjacent regions of the eye. Optimal dosage and modes of administration can readily be determined by conventional protocols. This treatment can: (a) decrease lymphocyte infiltration in adjacent lacrimal tissue and thereby alleviate immune-mediated destruction, and lymphocyte compression, of acinar and ductal cells; (b) permit accessory and/or palpebral lacrimal glands to secrete basal tear volumes; it is estimated that a tear secretion rate of only 0.1 µl/minute (i.e., one-tenth of normal) could maintain a stable tear film under favorable conditions (1); and (c) make available regions of functional lacrimal tissue, that might respond to exogenous tear stimulants to enhance surface volume.

Topical administration of androgens would avoid the numerous side effects of parallel systemic exposure to these hormones, including virilization, menstrual irregularities (e.g. amenorrhea), hepatic dysfunction, edema, hematologic abnormalities, behavioral changes and metabolic alterations. In addition, the therapeutic augmentation of basal tear secretion could allow the use of visual aids, such as contact lenses, in the Sjögren's syndrome or other autoimmune patient population.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

REFERENCES

1. Holly, F. J., Tear film physiology. Internat. Ophthalmol. Clin. 27:2–6 (1987).
2. Whitcher, J. P., Clinical diagnosis of the dry eye. Internat. Ophthalmol. Clin. 27:7–24 (1987).
3. Lamberts, D. W., Keratoconjunctivitis sicca. In "The Cornea. Scientific Foundations and Clinical Practice" (G. Smolin, and R. A. Thoft, Eds.), pp. 293–308, Little, Brown and Co, Boston, Mass. (1983).
4. Lemp, M. A., Recent developments in dry eye management. Ophthalmology 94:1299–1304 (1987).
5. Lubniewski, A. J., and Nelson, J. D., Diagnosis and management of dry eye and ocular surface disorders. Ophthalmol. Clin. N. A. 3:575–594 (1990).
6. Kaswan, R., Cyclosporine drops: a potential breakthrough for dry eye. Res. Prev. Blindness Writers Seminar, pp. 18–20 (1989).
7. Tabbara, K. F., Sjögren's Syndrome In "The Cornea. Scientific Foundations and Clinical Practice" (G. Smolin, and R. A. Thoft, Eds.), pp. 309–314, Little, Brown and Co, Boston, Mass. (1983).
8. Moutsopoulos, H. M., and Talal, N., Immunologic abnormalities in Sjögren's syndrome. In "Sjögren's Syndrome. Clinical and Immunological Aspects" (N. Talal, H. M. Moutsopoulos, and S. S. Kassan, Eds.), pp. 258–265, Springer Verlag, Berlin (1987).
9. Talal, N., and Moutsopoulos, H. M., Treatment of Sjögren's syndrome. In "Sjögren's Syndrome. Clinical and Immunological Aspects" (N. Talal, H. M. Moutsopoulos, and S. S. Kassan, Eds.), pp. 291–295, Springer Verlag, Berlin (1987).
10. Kincaid, M. C., The eye in Sjögren's syndrome. In "Sjögren's Syndrome. Clinical and Immunological Aspects" (N. Talal, H. M. Moutsopoulos, and S. S. Kassan, Eds.), pp. 25–33, Springer Verlag, Berlin (1987).
11. Daniels, T. E., and Talal, N., Diagnosis and differential diagnosis of Sjögren's syndrome. In "Sjögren's Syndrome. Clinical and Immunological Aspects" (N. Talal, H. M. Moutsopoulos, and S. S. Kassan, Eds.), pp. 193–199, Springer Verlag, Berlin (1987).
12. Daniels, T. T., Aufdemorte, T. B., and Greenspan, J. S., Histopathology of Sjögren's syndrome. In "Sjögren's Syndrome. Clinical and Immunological Aspects" (N. Talal, H. M. Moutsopoulos, and S. S. Kassan, Eds. ), pp. 41–52, Springer Verlag, Berlin (1987).
13. Alexander, E. L., Neuromuscular complications of primary Sjögren's syndrome. In "Sjögren's Syndrome. Clinical and Immunological Aspects" (N. Talal, H. M. Moutsopoulos, and S. S. Kassan, Eds.), pp. 61–82, Springer Verlag, Berlin (1987).
14. Daniels, T. E., Sjögren's syndrome–in a nut shell. Sjögren's Syndrome Foundation Inc. Report, Port Washington, N.Y. (1990).
15. Talal, N., and Ansar Ahmed, S., Sex hormones and autoimmune disease: a short review. Int. J. Immunotherapy 3:65–70 (1987).
16. Ansar Ahmed, S., Penhale, W. J., and Talal, N., Sex hormones, immune responses and autoimmune diseases. Am. J. Pathol. 121:531–551 (1985).
17. Burns, J. C., Persistent cytomegalovirus infection. The etiology of Sjögren's syndrome. Med. Hypotheses 10:451–460 (1983).
18. Fox, R. I., Pearson, G., and Vaughan, J. H., Detection of Epstein-Barr virus-associated antigens and DNA in salivary gland biopsies from patients with Sjögren's syndrome. J. Immunol. 137:3162–3168 (1986).
19. Pflugfelder, S. C., Tseng, S. C. G., Pepose, J. S., Fletcher, M. A., Klimas, N., and Feuer, W., Epstein-Barr virus infection and immunological dysfunction in patients with aqueous tear deficiency. Ophthalmology 97:313–323 (1990).
20. Pepose, J. S., Akata, R. F., Pflugfelder, S. C., and Voigt, W., Mononuclear cell phenotypes and immunoglobulin gene rearrangements in lacrimal gland biopsies from patients with Sjögren's syndrome. Ophthalmology 97:1599–1605 (1990).
21. Green, J. E., Hinrichs, S. H., Vogel, J., and Jay, G., Exocrinopathy resembling Sjögren's syndrome in HTLV-1 tax transgenic mice. Nature 341:72–74(?).
22. Garry, R. F., Fermin, C. D., Hart, D. J., Alexander S. S., Donehower, L. A., and Luo-Zhang, H., Detection of a human intracisternal A-type retroviral particle antigenically related to HIV. Science 250:1127–1129 (1990).
23. Fox, R., Epstein-Barr virus and human autoimmune diseases: possibilities and pitfalls. J. Vir. Meth. 21:19–27 (1988).

24. Maini, R. N., The relationship of Sjögren's syndrome to Rheumatoid Arthritis. In "Sjögren's Syndrome. Clinical and Immunological Aspects" (N. Talal, H. M. Moutsopoulos, and S. S. Kassan, Eds.), pp. 165–176, Springer Verlag, Berlin (1987).
25. Venables, P. J. W., Teo, C. G., Baboonian, C., Griffin, B. E., Hughes, R. A., and Maini, R. N., Persistence of Epstein-Barr virus in salivary gland biopsies from healthy individuals and patients with Sjögren's syndrome. Clin. Exp. Immunol. 75:359–364 (1989).
26. Tabbara, K. F., and Frayha, R. A., Alternate-day steroid therapy for patients with primary Sjögren's syndrome. Annals Ophthalmol. 15:358–361 (1983).
27. Prijot, E., Bazin, L., and Destexhe, B., Essai de traitment hormonal de la keratocon-jonctivite seche. Bull. Soc. Belge Ophtalmol. 162:795–800 (1972).
28. Drosos, A. A., Skopouli, F. N., Galanopoulou, K., Kitridou, R. C., and Moutsopoulos, H. M., Cyclosporin A therapy in patients with primary Sjögren's syndrome: results at one year. Scand. J. Rheum. Suppl. 61:246–249 (1986).
29. Nasu, M., Matsubara, O., and Yamamoto, H., Post-mortem prevalence of lymphocytic infiltration of the lacrymal gland: a comparative study in autoimmune and non-autoimmune diseases. J. Pathology 143:11–15 (1984).
30. Carlsten, H., Tarkowski, A., Holmdahl, R., and Nilsson, L. A., Oestrogen is a potent disease accelerator in SLE-prone MRL lpr/lpr mice. Clin. Exp. Immunol. 80:467–473 (1990).
31. Ahmed, S. A., Aufdemorte, T. B., chen, J. R., Montoya, A. I., Olive, d., and Talal, N., Estrogen induces the development of autoantibodies and promotes salivary gland lymphoid infiltrates in normal mice. J. Autoimmunity 2:543–552 (1989).
32. Frost-Larsen, K., Isager, H., and Manthorpe, R., Sjögren's syndrome treated with bromhexine: a randomized clinical study. Br. Med. J. 1:1579–1581 (1978).
33. Gilbard, J. P., Rossi, S. R., Heyda, K. G. and Dartt, D. A., Stimulation of tear secretion and treatment of dry-eye disease with 3-isobutyl-1-methylxanthine. Arch. Ophthalmol. 109:672–676 (1991).
34. Manthorpe, R., Petersen, S. H., and Prause, J. U., Mucosolvan in the treatment of patients with primary Sjögren's syndrome. Acta Ophthalmol. (Copenh) 62:537–541 (1984).
35. Kriegbaum, N. J., von Linstow, M., Oxholm, P., and Prause, J. U., A follow-up study of the progress of keratoconjunctivitis sicca and response to treatment in primary Sjögren's syndrome. Scand. J. Rheumatol. 18:193–196 (1989).
36. Raveche, E. S., and Steinberg, A. D., Sex hormones in autoimmunity. In "Pituitary Function and Immunity" (I. Berczi, Ed.), pp. 283–301, CRC Press, Boca Raton, Florida (1986).
37. Ahmed, S. A., and Talal, N., Sex hormones and the immune system-part 2. Animal data. Bailliere's Clin. Rheum. 4:13–31 (1990).
38. Roubinian, J. R., Talal, N., Greenspan, J. S., Goodman, J. R., and Siiteri, P. K., Effect of castration and sex-hormone treatment on survival, anti-nucleic acid antibodies, and glomerulonephritis in NZB/NZW F1 mice. J. Exp. Med. 147:1568–1583 (1978).
39. Melez, K. A., Boegel, W. A., and Steinberg, A. D., Therapeutic studies in New Zealand mice. VII. Successful androgen treatment of NZB/NZW F1 females of different ages. Arthritis Rheum. 23:41–47 (1980).
40. Nelson, J. L., and Steinberg A. D., Sex steroids, autoimmunity, and autoimmune diseases. In "Hormones and Immunity" (I. Berczi, and K. Kovacs, Eds.), pp. 93–119, MTP Press Limited, Lancaster, England (1987).
41. Shear, H. L., Wofsy, D. and Talal, N., Effects of castration and sex hormones on immune clearance and autoimmune disease in MRL/Mp-lpr/lpr and MRL/Mp-+/+ mice. Clin. Immunol. Immunopathol. 26:361–369 (1983).
42. Ansar Ahmed, S., Young, P. R., and Penhale, W. J., Beneficial effect of testosterone in the treatment of chronic autoimmune thyroiditis in rats. J. Immunol. 136:143–147 (1986).
43. Allen, J. B., Blatter, D., Calandrea, G. B., and Wilder, R. L., Sex hormonal effects on the severity of streptococcal cell wall induced polyarthritis in the rat. Arthritis Rheum. 26:560–565 (1983).
44. Ahn, Y. S., Harrington, W. J., Simon, S. R., Mylvagnam, R., Pall, L. M., and So, A. G., Danazol for the treatment of idiopathic thrombocytopenic purpura. N. Engl. J. Med. 308:1396–1399 (1983).
45. Sullivan, D. A., Hormonal influence on the secretory immune system of the eye. In "The Neuroendocrine-Immune Network" (I. Berczi, Ed.), pp. 199–238, CRC Press, Boca Raton, Fla., (1990).
46. MacDonald, T. T., Challacombe, S. J., Bland, P. W., Stokes, C. R., Heatley, R. V., McI Mowat, A., Eds, "Advances in Mucosal Immunology," pp. 1–948, Kluwer Academic Publishers, London, England (1990).
47. Ariga, H., Edwards, J., and Sullivan, D. A. Androgen control of autoimmune expression in lacrimal glands of MRL/Mp-lpr/lpr mice. Clinical Immunology and Immunopathology 53:499–508 (1989).
48. Vendramini, A. C, Soo, C. H., and Sullivan, D. A., Testosterone-induced suppression of autoimmune disease in lacrimal tissue of a mouse model (NZB/NZW F1) of Sjögren's Syndrome. Invest. Ophthalmol. Vis. Sci. 32:3002–3006 (1991).
49. Bizzarro, A., Valentini, G., Di Marinto, G., Daponte, A., De Bellis, A., and Iacono, G., Influence of testosterone therapy on clinincal and immunological features of autoimmune diseases associated with Klinefelter's syndrome. J. Clin. End. Metab. 64:32–36 (1987).
50. Hoffman, R. W., Alspaugh, M. A., Waggie, K. S., Durham, J. B., and Walker, S. E., Sjögren's syndrome in MRL/l and MRL/n mice. Arthritis Rheum. 27:157–165 (1984).
51. Jabs, D. A., Alexander, E. L., and Green, W. R., Ocular inflammation in autoimmune MRL/Mp mice. Invest. Ophthalmol. Vis. Sci. 26:1223–1229 (1985).
52. Kessler, H. S., A laboratory model for Sjögren's syndrome. Am. J. Pathol. 52:671–678 (1968).
53. Celenligil, H., Kansu, E., Ruacan, S., and Eratalay, K., Secretory immune system and mucosal immunohistology in Sjögren's syndrome. Adv. Exp. Biol. Med. 216B:1641–1648 (1987).
54. Drosos, A. A., Vliet-Dascalopoulou, E., Andonopoulos, A. P., Galanopoulou, V., Skopouli, F. N., and Moutsopoulos, H. M., Nandrolone decanoate (deca-durabolin) in primary Sjögren's syndrome: a double blind study. Clin. Exp. Rheum. 6:53–57 (1988).
55. Hene, R. J., Kruize, A., Kater, L., Gmelig, F. H. J., and Oei, H. Y., Lack of clinical effect of the androgenic steroid nandrolone on primary Sjögren's syndrome (PSS). Clin. Exp. Rheum. 9:338 (1991).
56. Steinberg, A. D., Roths, J. B., Murphy, E. D., Steinberg, R. T., and Raveche, E. S., Effects of thymectomy or androgen administration upon the autoimmune disease of MRL/Mp-lpr/lpr mice. J. Immunol. 125:871–873 (1980).

57. Brick, J. E., Walker, S. E., and Wise, K. S., Hormone control of autoantibodies to calf thymus nuclear extract (CTE) and DNA in MRL-lpr and MRL-+/+ mice. Clin. Immunol. Immunopathol. 46:68–81 (1988).
58. Jabs, DA, and Prendergast, RA: Murine models of Sjögren's syndrome. Invest Ophthalmol Vis Sci 29:1437 (1988).
59. Jonsson, R. L., Tarkowski, A., Backman, K., and Klareskog, L., Immunohistochemical characterization of sialadenitis in NZB x NZW F1 mice. Clin. Immunol. Immunopathol. 42:93–101 (1987).
60. Connolly, K. M., Stcher, V. J., Snyder, B. W., Bohnet, E., and Potts, G. O., The effect of danazol in the MRL/lpr mouse model of autoimmune disease. Agents Actions 25:164–170 (1988).
61. Mountz, J. D., Smith, H. R., Wilder, r. L., Reeves, J. P., and Steinberg, A. D., CS-A therapy in MRL-lpr/lpr mice: amelioration of immunopathology despite autoantibody production. J. Immunol. 138:157–163 (1987).
62. Hazelton, R. A., McCruden, A. B., Sturrock, R. D., and Stimson, W. H., Hormonal manipulation of the immune response in systemic lupus erythematosus: a drug trial of an anabolic steroid, 19-nortestosterone. Annals Rheum. Dis. 42:155–157 (1983).
63. Lahita, R., Sex hormones, Sjögren's syndrome and the immune response. The Moisture Seekers Newsletter 8:1 (1991).
64. Comsa, J., Leonhardt, H., and Wekerle, H., Hormonal Coordination of the immune response, Rev. Physiol. Biochem. Pharmacol. 92:115–191 (1982).
65. Grossman, C. J., Regulation of the immune system by sex steroids, Endocr. Rev., 5:435–455 (1984).
66. Munck, A., Guyre, P. M. and Holbrook, N. J., Physiological functions of glucocorticoids in stress and their relation to pharmacological actions, Endocr. Rev., 5:25–44 (1984).
67. Besedovsky, H. O., del Rey, A. E. and Sorkin, E., Immune-neuroendocrine interactions, J. Immunol., 135:750–754 (1985).
68. Berczi, I., Pituitary Function and Immunity, pp. 1–347, CRC Press, Boca Raton, Fla. (1986).
69. Berczi, I. and Kovacs, K., Hormones and Immunity, pp. 1–332, MTP Press, Ltd., Lancaster, England (1987).
70. Jancovik, B. D., Markovic, B. M., and Spector, N. H., Neuroimmune Interactions, Ann. N.Y. Acad. Sci. 496, New York Acad. Sci., New York (1987).
71. Weigent D. A., Blalock J., Interactions between the neuroendocrine and immune systems: common hormones and receptors. Immunol Rev 100:79–108 (1987).
72. Freier, S., Ed., "The Neuroendocrine-Immune Network", pp. 1–266, CRC Press, Boca Raton, Fla. (1990).
73. Hadden, J. W., Masek, K., Nistico, G., Eds., "Interactions Among Central Nervous System, Neuroendocrine and Immune Systems," pp. 1–464, Pythagora Press, Rome (1989).
74. Ader, R., Felten, D. L., Cohen, N., Eds., "Psychoneuroimmunology, 2nd Edition," pp. 1–1248, Academic Press, San Diego, Calif. (1991).
75. Ader, R., Felten, D., Cohen, N., Interactions between the brain and immune system. Annu Rev Pharmacol. Toxicol. 30:561–602 (1990).
76. Stead, R. H., J. Bienenstock, and A. M. Stanisz., Neuropeptide regulation of mucosal immunity. Immunol. Rev. 100:333–359 (1987).
77. Golsteyn, E. J., and Fritzler, M. J., Review: The role of the thymic-hypothalamus-pituitary-gonadal axis in normal immune processes and autoimmunity. J. Rheum. 14:982–990 (1987).
78. Physicians' Desk Reference, 46th edition. Medical Economics Data, Montvale, N.J. (1992).
79. Andrews, B. S., Eisenberg, R. A., Theofilopoulos, A. N., Izui, S., Wilson, C. B., McConahey, P. J., Murphy, E. D., Roths, J. B., and Dixon, F. J., Spontaneous murine lupus-like syndromes: Clinical and immunopathological manifestations in several strains. J. Exp. Med. 149:1198–1215 (1978).
80. Theofilopoulos, A. N., and Dixon, F. J., Murine models of systemic lupus erythematosus. Adv. Immunol. 37:269–390 (1985).
81. Gelfand, J. A., Sherins, R. J., Alling, D. W., and Frank, M. M., Treatment of hereditary angioedema with danazol. New Eng. J. Med. 295:1444–1448 (1976).
82. Jonsson, R., Tarkowski, A., and Backman, K., Effects of immunomodulating treatment on autoimmune sialadenitis in MRL/Mp-lpr/lpr mice. Agents Actions 25:368–374 (1988).
83. Smith, H. R., Chused, T. M., and Steinberg, A. D., Cyclophosphamide-induced changes in the MRL-lpr/lpr mouse: Effects upon cellular composition, immune function and disease. Clin. Immunol. Immunopathol. 30:51–61 (1984).
84. Shiraki, M., Fujiwara, M., and Tomura, S., Long term administration of cyclophosphamide in MRL/l mice. I. The effects on the development of immunological abnormalities and lupus nephritis. Clin. Exp. Immunol. 55:333–339 (1984).
85. Bartlett, R. R., Popovic, S., and Raiss, R. X., Development of autoimmunity in MRL/lpr mice and the effects of drugs on this murine disease. Scand. J. Rheumatol. Suppl. 75:290–299 (1988).
86. Wilson, J. D., and Foster, D. W., eds., "Williams Textbook of Endocrinology," WB Saunders Company, Philadelphia (1985).
87. Knepper, P. A., Collins, J. A., and Frederick, R., Effect of dexamethasone, progesterone, and testosterone on IOP and GAGs in the rabbit eye. Invest. Ophthalmol. Vis. Sci. 26:1093–1100 (1985).
88. Vida, J. A., "Androgens and Anabolic Agents," Academic Press, New York (1969).
89. Cavallero, C., Relative effectiveness of various steroids in an androgen assay using the exorbital lacrimal gland of the castrated rat. Acta Endocrinol. (Copenh.), 55:119–131 (1967).

What is claimed is:

1. A method for treating keratoconjunctivitis sicca (KCS) comprising providing a therapeutic agent comprising a therapeutically effective amount of an androgen or androgen analogue that has androgenic effectiveness and not estrogen effectiveness in topical application, said androgen or androgen analogue being in a pharmaceutically acceptable substance, and administering said therapeutic agent topically to the ocular surface or immediate vicinity of an eye of a patient.

2. The method of claim 1 wherein in said administering step, said therapeutic agent is applied to the ocular surface of the eye.

3. The method of claim 1 wherein in said administering step, said therapeutic agent is applied to a region of the eye adjacent the ocular surface.

4. The method of claim 1 wherein in said providing step, said pharmaceutically acceptable substance comprises hyaluronate.

5. The method of claim 1 wherein in said providing step, said pharmaceutically acceptable substance comprises phosphate buffered saline.

6. The method of claim 1 wherein said androgen or androgen analogue is from a structural subclass of androgens comprising androgenic compounds with unusual structural features.

7. The method of claim 6 wherein said androgen or androgen analogue is 17α-methyl-17β-hydroxy-2-oxa-5α-androstan-3-one.

8. The method of claim 1 wherein said androgen or androgen analogue is a testosterone derivative.

9. The method of claim 1 wherein said androgen or androgen analogue is a 4,5α-dihydrotestosterone derivative.

10. The method of claim 1 wherein said androgen or androgen analogue is a 17β-hydroxy-5α-androstane derivative containing a ring A unsaturation.

11. The method of claim 1 wherein said androgen or androgen analogue is a 19-nortestosterone derivative.

12. The method of claim 1 wherein said androgen or androgen analogue is a nitrogen-substituted androgen.

* * * * *

(12) REEXAMINATION CERTIFICATE (4250th)
United States Patent
Sullivan

(10) Number: US 5,620,921 C1
(45) Certificate Issued: Jan. 9, 2001

(54) OCULAR ANDROGEN THERAPY IN SJOGREN'S SYNDROME

(75) Inventor: David A. Sullivan, Acton, MA (US)

(73) Assignee: The Schepens Eye Research Institute, Inc., Boston, MA (US)

Reexamination Request:
No. 90/004,856, Dec. 2, 1997

Reexamination Certificate for:
Patent No.: 5,620,921
Issued: Apr. 15, 1997
Appl. No.: 08/124,842
Filed: Sep. 21, 1993

Related U.S. Application Data

(63) Continuation of application No. 07/871,657, filed on Apr. 21, 1992, now abandoned.

(51) Int. Cl.$^7$ ................................................ A61K 31/56
(52) U.S. Cl. ................................................ 514/178; 514/912
(58) Field of Search ................................ 514/178, 912

(56) References Cited

U.S. PATENT DOCUMENTS 5,041,434    8/1991    Lubkin .............................. 514/182

*Primary Examiner*—Zohreh Fay

(57) ABSTRACT

The topical application to the ocular surface or adjacent regions of the eye of a preparation containing a therapeutic amount of an androgen or androgen analogue is disclosed as a method of relieving the chronic and acute manifestation of dry eye symptoms in Sjögren's syndrome.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2–12, dependent on an amended claim, are determined to be patentable.

1. A method for treating keratoconjunctivitis sicca (KCS) *due to androgen deficient disorders and not caused by estrogen deficiency, said method* comprising
   providing a therapeutic agent comprising a therapeutically effective amount of an androgen or androgen analogue that has androgenic effectiveness and not estrogen effectiveness in topical application, said androgen or androgen analogue being in a pharmaceutically acceptable substance, and
   administering said therapeutic agent topically to the ocular surface or immediate vicinity of an eye of a patient.

* * * * *